US006720564B1

(12) United States Patent
Koch

(10) Patent No.: US 6,720,564 B1
(45) Date of Patent: Apr. 13, 2004

(54) METHOD AND APPARATUS FOR FINGERPRINT DETECTION AND ANALYSIS

(75) Inventor: Charles H. Koch, Storrs, CT (US)

(73) Assignee: The University of Connecticut, Storrs, CT (US)

( * ) Notice: Subject to any disclaimer, the term of this patent is extended or adjusted under 35 U.S.C. 154(b) by 0 days.

(21) Appl. No.: 10/310,233

(22) Filed: Dec. 5, 2002

(51) Int. Cl.[7] .................................................. G06K 9/00
(52) U.S. Cl. .............................. 250/492.21; 250/492.1; 250/492.3; 250/306; 250/310; 427/1
(58) Field of Search .................... 250/492.21, 492.1, 250/492.3, 306, 310; 427/1

(56) References Cited

U.S. PATENT DOCUMENTS 6,234,031 B1 * 5/2001 Suga ...................... 73/862.474

OTHER PUBLICATIONS

Abstract—"Forensic Applications of Ion Beam Mixing and Surface Spectroscopy Of Latent Fingerprints"; published on or about Jul. 30, 2001 in the Proceedings Of SPIE (International Society for Optical Engineering); Conference held Jul. 30–31, 2001, San Diego, CA.

Published by Oak Ridge National Labs, SIMS and tandem mass spec techniques combine to form a promising analytical and diagnostic tool, Oct. 2, 2003, UCONN Article, (4 pgs.).

* cited by examiner

Primary Examiner—Nikita Wells
(74) Attorney, Agent, or Firm—Cantor Colburn LLP

(57) ABSTRACT

A method of detecting fingerprints on a substrate includes ion beam mixing materials associated with the fingerprint into the substrate to create an ion beam mixed fingerprint; and analyzing the ion beam mixed fingerprint. Analyzing the ion beam mixed fingerprint may include optical imaging, scanning with a scanning electron microscope, or performing a surface analysis technique on the ion beam mixed fingerprint to identify the chemical composition of at least one material in at least one of the fingerprint and the substrate. In one aspect, the surface analysis technique includes at least one of Auger Spectroscopy, Secondary Ion Mass Spectroscopy (SIMS), Secondary Electron Microscopy (SEM), Particle Induced X-ray Emission (PIXE), and Energy Dispersive X-ray Spectroscopy (EDS). The analyzing may further include mapping the chemical composition of the at least one material in the at least one of the fingerprint and the substrate to produce a computer generated image of the fingerprint. The mass (ion species), fluence, and energy of the incident ion beam for various substrates are provided.

70 Claims, 8 Drawing Sheets

METHOD AND APPARATUS FOR FINGERPRINT DETECTION AND ANALYSIS

BACKGROUND

The present invention is related to the field of forensic science. More particularly, the present invention is related to fingerprint detection and analysis.

Fingerprints are impressions of the system of friction ridges on the surface of fingers, palms, toes, and feet. Most latent fingerprints are formed when perspiration escapes through the ridged surface. The primary component of such a fingerprint is ordinary perspiration. Human perspiration is a mixture of many substances including fatty acids, proteins, peptides, amino acids, chloride salts, water, and urea, some of which can remain detectable on a surface for long periods of time. Fingerprints can also contain residue of what a person has handled. For example, if a person was handling grease, gasoline, TNT, or other substances, the fingerprint may contain trace amounts of these substances.

A variety of methods have been developed which use the various substances contained in the residues of a latent fingerprint for creating an observable image. For example, silver nitrate was found to react with the salt in a latent print, which, through exposure to a light source, forms a visible fingerprint image.

The method widely known as "dusting for prints" involves depositing a colored powder on a surface suspected of bearing latent fingerprints. The powder adheres to lipid residue on a surface and the loose excess powder is delicately brushed off, thereby disclosing any latent fingerprints.

In another method, iodine crystals are warmed causing the sublimation of the crystals and the gas thus produced is blown or wafted over the surface being examined for latent fingerprints. Iodine gas reacts with the lipids, causing the latent fingerprint to become visible.

Recent developmental work in the field of fingerprint detection has yielded new detection methods including various fluorogenic visualization and cyanoacrylate (C/A) fuming techniques. In the fluorogenic visualization techniques, the latent fingerprint is treated with one or more chemical reagents which react with and covalently bond with compounds in the print to form a fluorescent chemical product. The image of the latent print is then viewed or photographed with the aid of an optical filter and under illumination of light of appropriate wavelength to cause excitation and fluorescence of the image.

Each of these fingerprint detection techniques relies on the presence of residues from perspiration, which must be present in sufficient quantity to perform the technique. After the sufficient quantity of residue is removed from the surface, the technique can no longer be performed. While more modern techniques require only a small amount of residue, there is still a need for a fingerprint detection technique that would reduce the amount of residue needed to detect latent fingerprints.

Once detected, the fingerprints must be preserved for analysis. One method of preserving the fingerprint is by "lifting" the fingerprint from the surface using tape or other material. Another method of preserving the fingerprint is by photographing the fingerprint. While both methods are sufficient for macro analyses by human experts, such as the detection of whorls, arches, and loops, the resolution of the preserved fingerprint is typically not sufficient for use with sophisticated computer algorithms for analyzing micro features of the fingerprint.

SUMMARY OF THE INVENTION

The above-described drawbacks and deficiencies of the prior art are overcome or alleviated by a method of detecting fingerprints on a substrate, the method comprising: ion beam mixing materials associated with the fingerprint into the substrate to create an ion beam mixed fingerprint; and analyzing the ion beam mixed fingerprint.

In one embodiment, analyzing the ion beam mixed fingerprint includes optically imaging the ion beam mixed fingerprint. In another embodiment, the analyzing includes scanning the ion beam mixed fingerprint with a scanning electron microscope. In another embodiment, the analyzing includes performing a surface analysis technique on the ion beam mixed fingerprint to identify the chemical composition of at least one material associated with at least one of the fingerprint and the substrate.

In one aspect, the surface analysis technique includes at least one of Auger Spectroscopy, Secondary Ion Mass Spectroscopy (SIMS), Secondary Electron Microscopy (SEM), Particle Induced X-ray Emission (PIXE), and Energy Dispersive X-ray Spectroscopy (EDS).

The analyzing may further include mapping the chemical composition of the at least one material associated with the at least one of the fingerprint and the substrate to produce a computer generated image of the fingerprint. The mapping may include identifying an element in the chemical composition of the at least one material associated with the at least one of the fingerprint and the substrate; and assigning pixel intensities to the relative abundance of the element.

These and other features and advantages of the present invention will be apparent from the following brief description of the drawings, detailed description, and appended claims and drawings.

BRIEF DESCRIPTION OF THE DRAWINGS

The invention will be further described in connection with the accompanying drawings in which.

DETAILED DESCRIPTION

The method and apparatus described herein employ an ion implantation process to ion beam mix the materials of latent fingerprints into a substrate, such that the atoms that form the latent fingerprints become an integrated part of the substrate material. The permanent record of the fingerprint can be imaged optically or with a scanning electron microscope. In addition, surface analysis techniques such as Auger Spectroscopy, Secondary Ion Mass Spectroscopy (SIMS), Secondary Electron Microscopy (SEM), Particle Induced X-ray Emission (PIXE), and Energy Dispersive X-ray Spectroscopy (EDS) can be used to identify the chemical composition of the fingerprint material.

Once identified, the materials of the fingerprint (e.g., elements, molecular fragments and/or molecules) unique to the fingerprint can be mapped using computer assigned intensities to their relative abundance. The result is a computer-aided map of the latent fingerprint drawn with elements, molecules or molecular fragments. These can be of human origin or residue from the person leaving the fingerprint.

Ion Implantation

Figure 1:
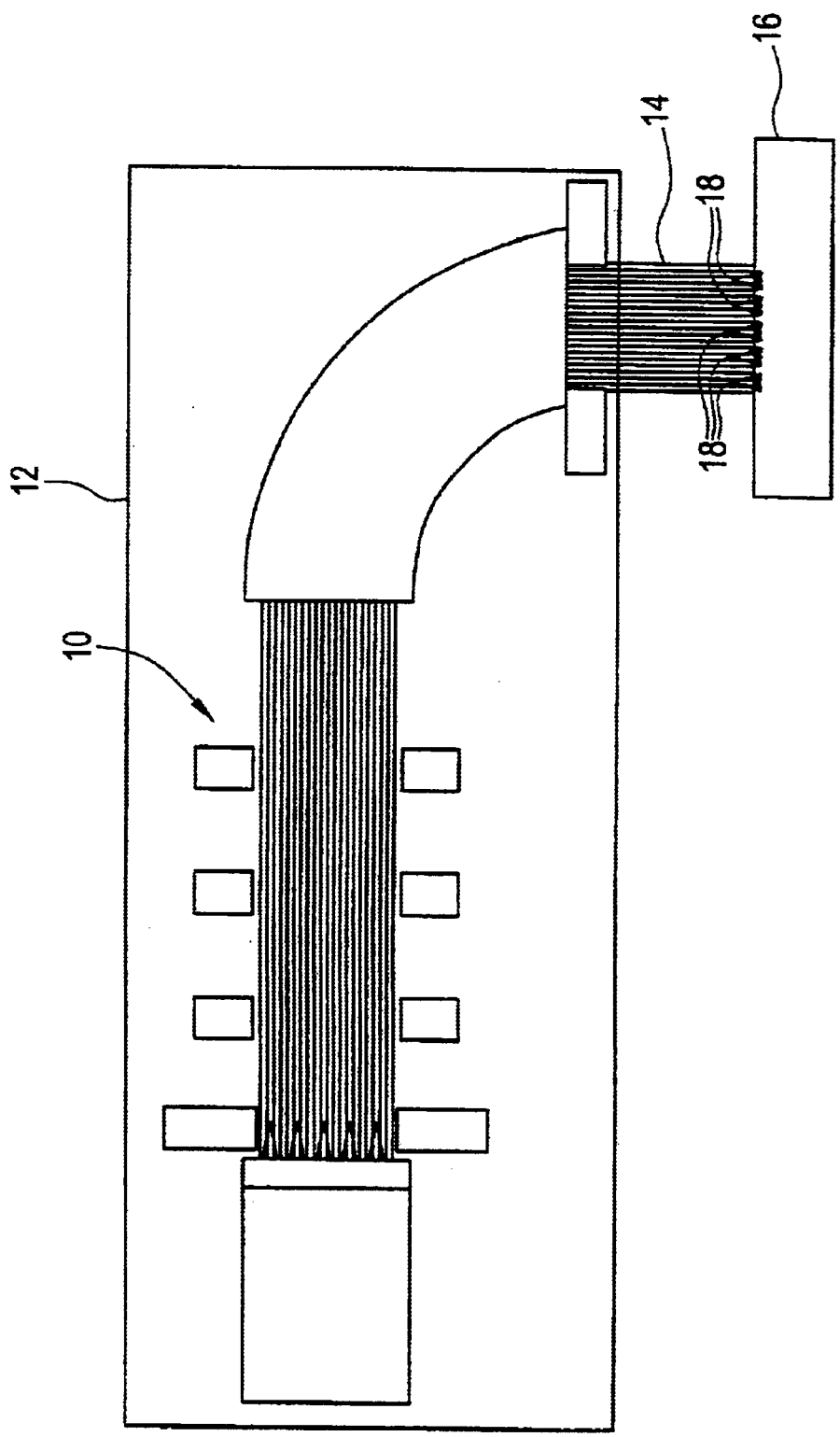
FIG. 1 illustrates a schematic of a system for ion beam mixing of a fingerprint into a substrate.

The first part of the method is to ion beam mix materials associated with a latent fingerprint into a substrate with the proper ion species, at the proper energy, and to the correct fluence. As shown in FIG. 1, a linear accelerator 10 within an ion implanter 12 to creates a beam of charged atoms, or ions 14. Within the ion implanter 12, the ion beam 14 is shaped and directed toward a substrate 16, and the ions are embedded in the material of the substrate 16. When the surface of the substrate 16 has material on it, such as a fingerprint 18, the effect of the incident ions is to drive that material into the surface of the substrate 16.

Figure 2:
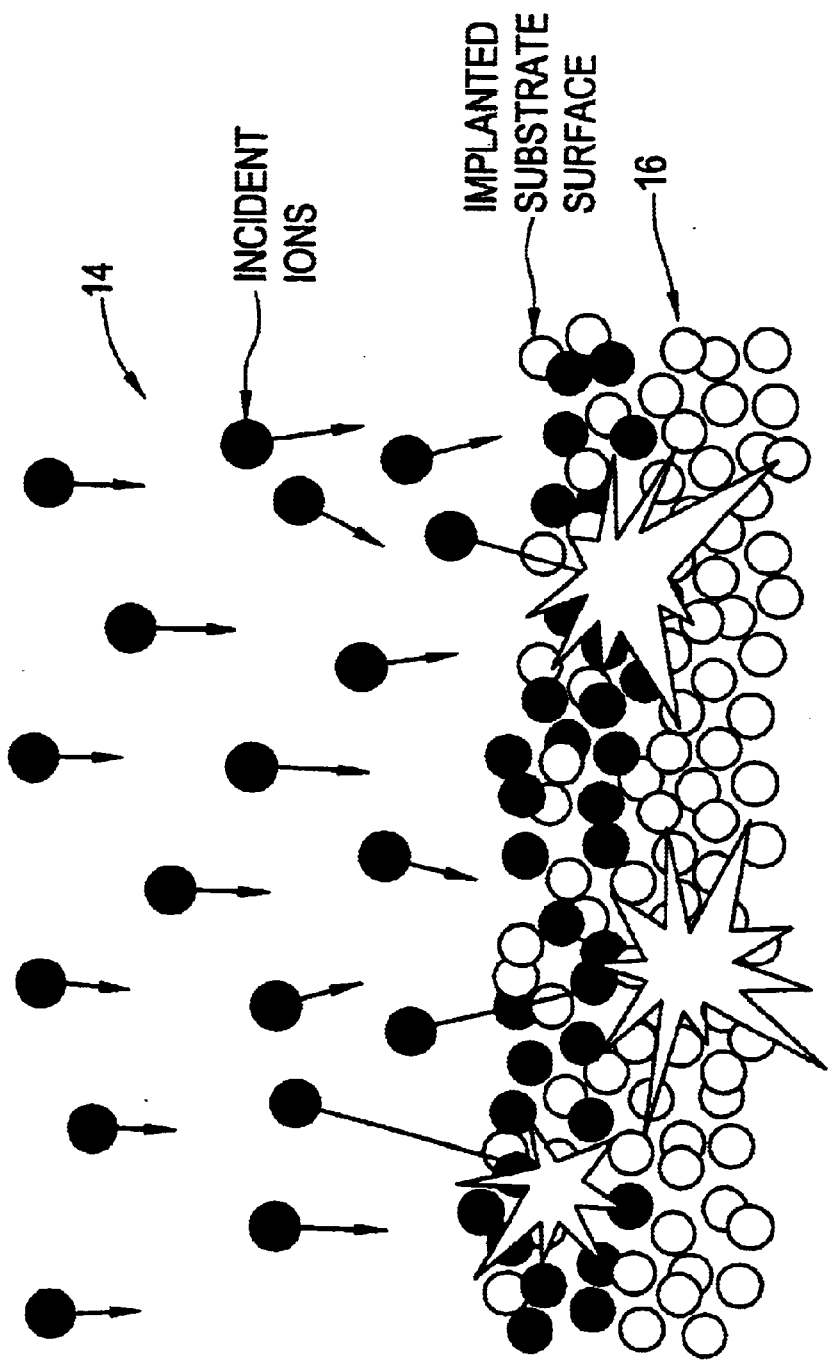
FIG. 2 illustrates the ion implantation process.

FIG. 2 illustrates the role of the incident beam 14 ions and how they are implanted into the substrate 16 surface. Energetic ions penetrate the surface and interact with the substrate 16 material. The composition and structure of the near surface region of the substrate 16 is altered. On the order of 1000 atoms are displaced from their lattice position by the collision cascade produced by one incoming energetic ion. This process in referred to as "ion beam mixing".

The ion implanter 12 may be any ion implanter such as, for example, those commercially available from companies such as Varian Semiconductor Equipment Associates, Inc. and Eaton and configured to provide a pure, focused ion beam of the appropriate mass (ion species), fluence, and energy for the substrate material, as described in further detail hereinafter.

For ion beam mixing of the fingerprint to be successful, the mass (ion species), fluence, and energy of the incident ion beam 14 should be matched to the substrate 16 on which the fingerprint 18 is formed. If the incident ion has too high a mass with too low an energy it will sputter the fingerprint 18 away, without any mixing taking place. If the incident ion is too low in mass, and too high in energy, it will pass through the fingerprint 18 and deposit its energy deep in the substrate 16. For optimal results the ion beam 14 should have the correct mass and energy and fluence to come to rest in the area of the interface between the fingerprint 18 and its substrate 16 material. Because the ions' final resting place is always a Gaussian distribution, some of the atoms from the fingerprint 18 will be carried into the substrate 16 material and remain there.

For metal substrates 16 the ion beam 14 is formed of a reactive element, preferably oxygen (e.g., O+ or $O_2$+) or chlorine. The ion beam 14 preferably has an energy greater than or equal to about 25 kilo electron volts (keV), more preferably greater than or equal to about 40 keV, and most preferably greater than or equal to about 50 keV. The ion beam 14 energy is preferably less than or equal to about 200 keV, more preferably less than or equal to about 100 keV, and most preferably less than or equal to about 75 keV. The ion beam 14 preferably has a fluence of greater than or equal to about $1\times10^{11}$ ions per square centimeter (cm), and more preferably greater than or equal to about $1\times10^{16}$ ions per square cm. The ion beam 14 preferably has a fluence less than or equal to about $1\times10^{19}$, more preferably less than or equal to about $1\times10^{17}$, and most preferably less than or equal to about $5\times10^{16}$ ions per square cm.

For polymer substrates 16 the ion beam 14 is preferably formed of an element having a cross section smaller than that of argon, preferably a chlorine element (e.g., Cl+). The ion beam 14 preferably has an energy greater than or equal to about 35 keV. The ion beam energy is preferably less than or equal to about 200 keV, more preferably less than or equal to about 100 keV, and most preferably less than or equal to about 50 keV. The ion beam 14 preferably has a fluence of greater than or equal to about $1\times10^{11}$ ions per square cm, and more preferably greater than or equal to about $1\times10^{15}$ ions per square cm. The ion beam 14 preferably has a fluence less than or equal to about $5\times10^{19}$, and more preferably less than or equal to about $5\times10^{16}$ ions per square cm.

For glass substrates 16 the ion beam 14 is preferably formed of an element having a cross section smaller than that of xenon, preferably a lithium element (e.g., Li). The ion beam 14 preferably has an energy greater than or equal to about 40 keV, and more preferably greater than or equal to about 50 keV. The ion beam energy is preferably less than or equal to about 200 keV, more preferably less than or equal to about 100 keV. The ion beam 14 preferably has a fluence of greater than or equal to about $5\times10^{11}$ ions per square cm, more preferably greater than or equal to about $5\times10^{16}$ ions per square cm, and most preferably greater than or equal to about $1\times10^{17}$ ions per square cm. The ion beam preferably 14 has a fluence less than or equal to about $5\times10^{19}$, more preferably less than or equal to about $5\times10^{17}$ ions per square cm, and most preferably less than or equal to about $2\times10^{17}$ ions per square cm.

For paper substrates 16 the ion beam 14 is preferably formed of an element having a cross section smaller than that of argon, preferably a lithium element (e.g., Li). The ion beam 14 preferably has an energy greater than or equal to about 30 keV. The ion beam 14 energy is preferably less than or equal to about 200 keV, more preferably less than or equal to about 70 keV. The ion beam 14 preferably has a fluence of greater than or equal to about $1\times10^{11}$ ions per square cm, and more preferably greater than or equal to about $1\times10^{15}$ ions per square cm. The ion beam 14 preferably has a fluence less than or equal to about $1\times10^{19}$, and more preferably less than or equal to about $1\times10^{16}$ ions per square cm.

The present invention uses this ion beam mixing process to imbed the latent fingerprint 18 material into the substrate 16 material. The fingerprint 18 is no longer only on the surface, but is now a permanent part of the substrate 16 material. The ion beam mixed fingerprint 18 extends in three dimensions into the substrate 16, with its size and shape corresponding to the size and shape of the fingerprint 18 when it was on the surface of the substrate 16. The ion implantation process takes what once was volatile and fragile fingerprint 18 material and imbeds those atoms and molecules into the substrate 16 making them more durable, permanent, and detectable by sophisticated material analysis techniques. For many substrates 16, the fingerprint 18, which may have been invisible (optically clear) on the surface of substrate 16, becomes visible (optically opaque) to the eye or to other optical imaging techniques after the ion beam mixing.

The second part of the method is to analyze the ion beam mixed fingerprint using one or more analysis method. Analysis of the ion beam mixed fingerprint can include optical imaging, such as viewing the fingerprint by eye or by using an optical microscope with or without a camera. Analysis of the ion beam mixed fingerprint may also include viewing the ion beam mixed fingerprint using a scanning electron microscope. Analysis of the ion beam mixed fingerprint can also be performed with computer aided, atomic/chemical mapping surface analysis techniques. This process allows the detection of the atoms and molecules left by the fingerprint 18. These analysis techniques use energetic ion or electron beams that would destroy or disassociate the fingerprint atoms and/or molecules if they were not ion beam mixed into the substrate 16 first. Examples of surface analysis techniques that may be used in this method are Auger Spectroscopy, Secondary Ion Mass Spectroscopy (SIMS), Secondary Electron Microscopy (SEM), Particle Induced X-ray Emission (PIXE), and Energy Dispersive X-ray Spectroscopy (EDS). These surface analysis techniques are discussed below.

Auger Spectroscopy

In a fist embodiment, the Auger electron spectroscopy technique is used to analyze the ion beam mixed fingerprint. The Auger electron spectroscopy technique for chemical analysis of surfaces is based on the Auger process. In general, when a core level of a surface atom is ionized by an impinging electron beam, the atom may decay to a lower energy state through an electronic rearrangement which leaves the atom in a double ionized state. The energy difference between these two states is given to the ejected Auger electron, which will have a kinetic energy characteristic of the parent atom. When the Auger transitions occur within a few angstroms of the surface, the Auger electrons may be ejected from the surface without loss of energy and give rise to peaks in the secondary electron energy distribution function. The energy and shape of these Auger features can be used to unambiguously identify the composition of the substrate 16 surface. By applying the Auger electron spectroscopy technique to the substrate 16, the atoms and molecules of the fingerprints 18, which have been ion beam mixed with the substrate 16, can be detected. A computer image of the fingerprint 18 can then be produced by assigning pixel intensities to the relative abundance of one or more selected compositional elements, molecules, or molecular fragments.

Figure 3:
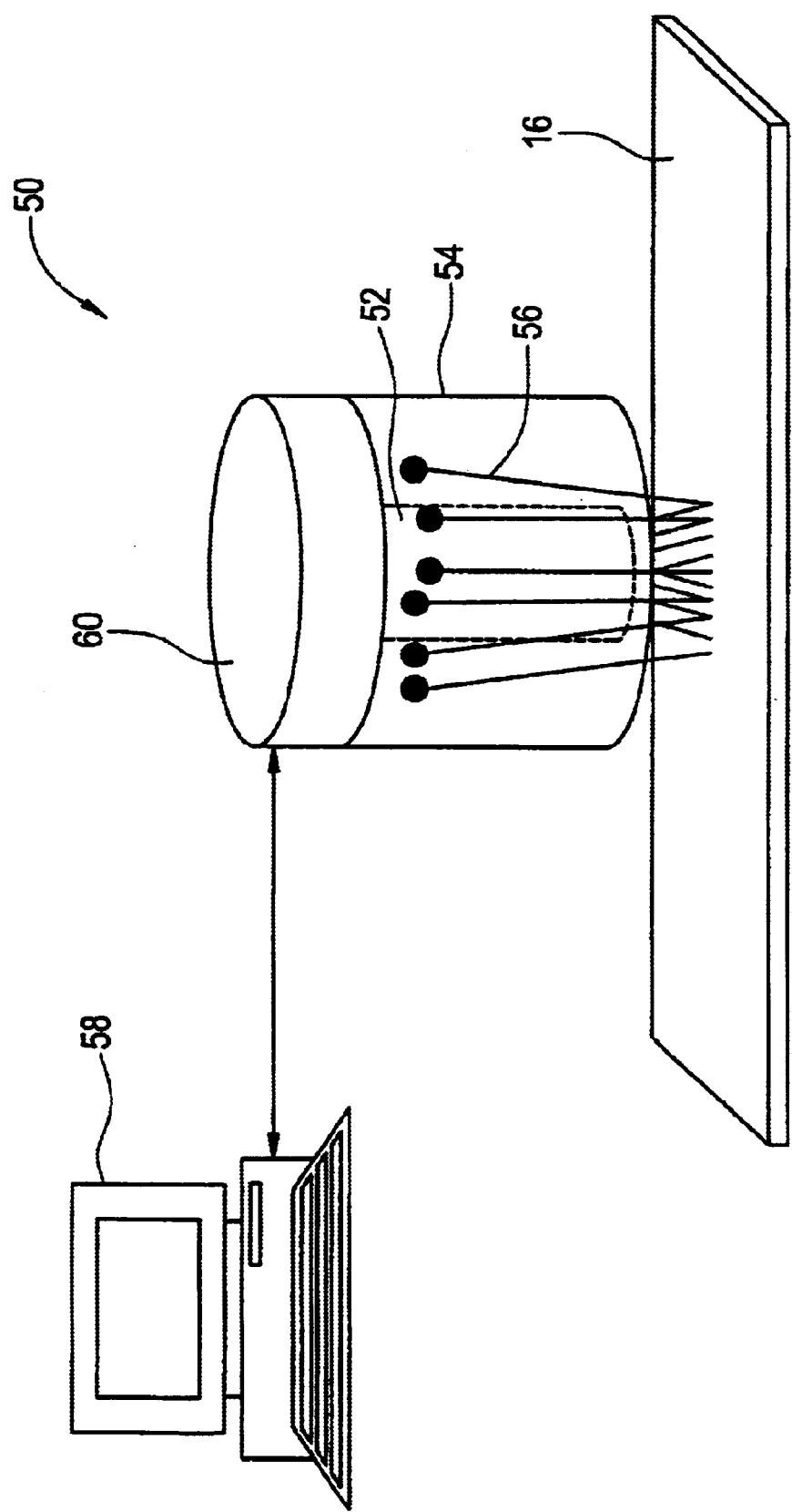
FIG. 3 illustrates a schematic of an Auger electron spectroscopy system.

Referring to FIG. 3, an Auger electron spectroscopy system 50 is shown. System 50 may be an ultrahigh vacuum system, which includes an electron gun 52 for substrate 16 excitation, and a cylindrical mirror analyzer, a double pass analyzer or any other detector 54 for the detection of Auger electrons 56 emitted from the substrate 16 for the acquisition of spectra. System 50 also includes a computer 58 configured to receive signals indicative of Auger electron energy from an electron multiplier 60 portion of the cylindrical mirror analyzer 54.

Because the Auger peaks are superimposed on a rather large continuous background, they are more easily detected by differentiating the kinetic energy distribution function N(E). Thus the conventional Auger spectrum is the function dN(E)/dE. Electron differentiation is readily accomplished with a velocity analyzer by superimposing a small AC voltage on the energy selecting voltage and synchronously detecting the output of the electron multiplier 60. The peak-to-peak magnitude of an Auger peak in a differentiated spectrum generally is directly related to the surface concentration of the element, which produces the Auger electrons 56. Quantitative analysis may be accomplished by comparing the peak heights obtained from an unknown specimen with those from pure elemental standards or from compounds of known composition.

Software associated with computer 58 provides computer 58 with the ability to acquire digital chemical mapping of elements from their Auger peak intensities. The software also allows small points chosen from a digitally collected Secondary Electron Detector (SED) image to be analyzed. In an exemplary embodiment, system 50 includes a commercially available Physical Electronics (PHI) Model 595 Scanning Auger Spectrometer, modified with a commercially available RBD Enterprises, Inc. model 137 computer control. Also, computer 58 may include commercially available RBD Enterprises, Inc. AugerScan software, which maps element peaks, and AugerMap software, which provides an image of surface chemistry (e.g., an image of the fingerprint 18). It will be appreciated that other commercially available components may be used for the same purpose.

Using the ion beam mixing method described above, sample fingerprints have been implanted and photographed. These samples have also been analyzed in an Auger spectrometer. This was done to determine elements present on the substrate in the fingerprint area after ion implantation. With this information it was possible to produce a computer generated map of the fingerprint using atomic concentrations of an indicator element found to be unique in the fingerprint lines.

Figure 4:
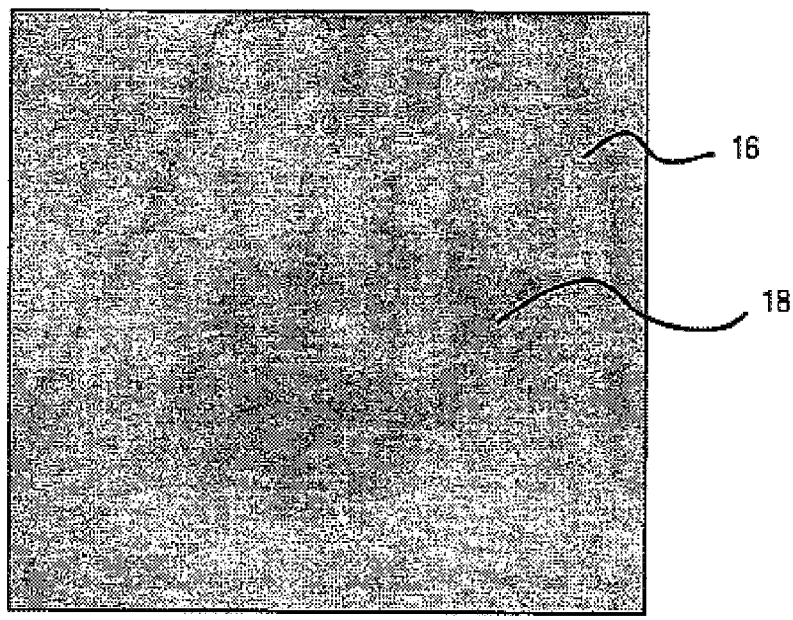
FIG. 4 illustrates enhanced fingerprints on a glass slide.

FIG. 4 illustrates enhanced fingerprint 18 on a glass substrate 16 as a result of the ion implantation process described above. The fingerprint material was ion beam mixed into the glass substrate. After implantation, the fingerprint 18 was not only a dark violet, but it could be rubbed or scratched with tweezers without smearing. The slide was placed in Auger electron spectroscopy system 50. It could now be imaged with secondary electrons. An image of one area was maintained for hours without any apparent loss of degradation. This would not have been possible without the ion beam mixing process. Micro features of the fingerprint 18 were then available for analysis.

Figure 5:
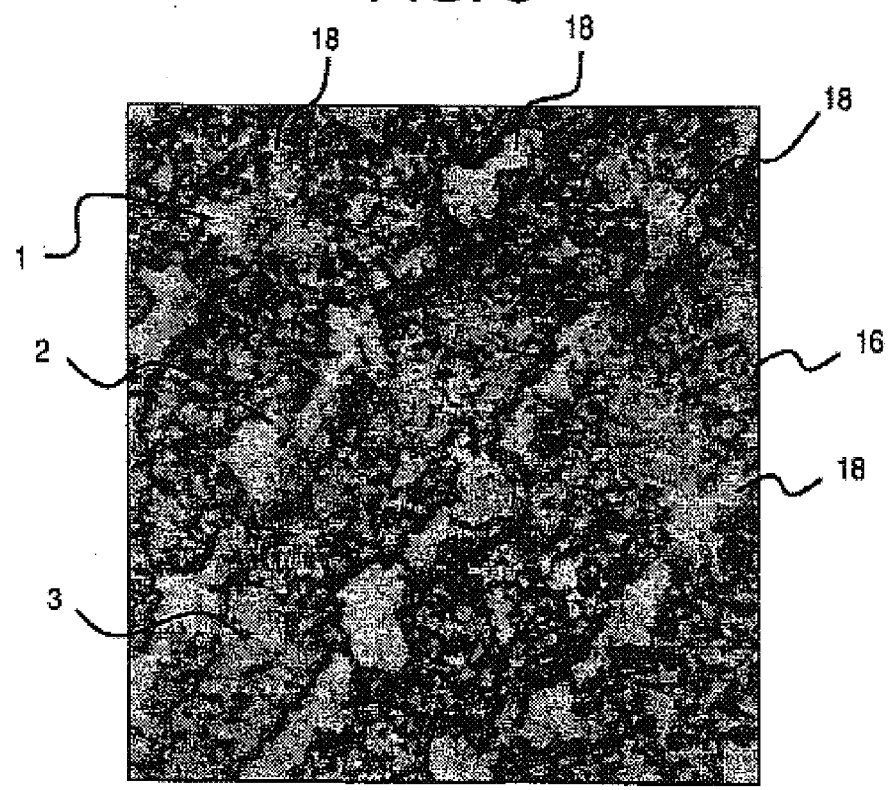
FIG. 5 illustrates secondary electron image of implanted fingerprint showing three areas analyzed.
Figure 6:
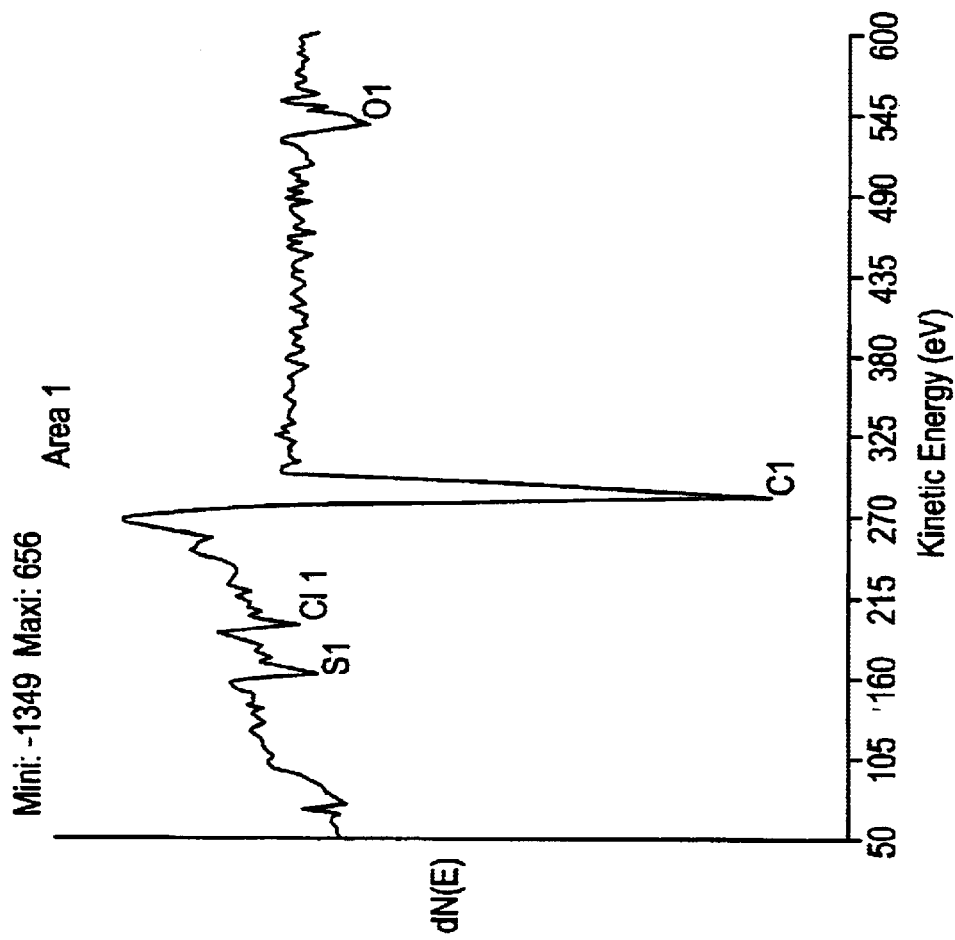
FIG. 6 illustrates an Auger scan of area 1 of FIG. 5 from implanted fingerprints.
Figure 7:
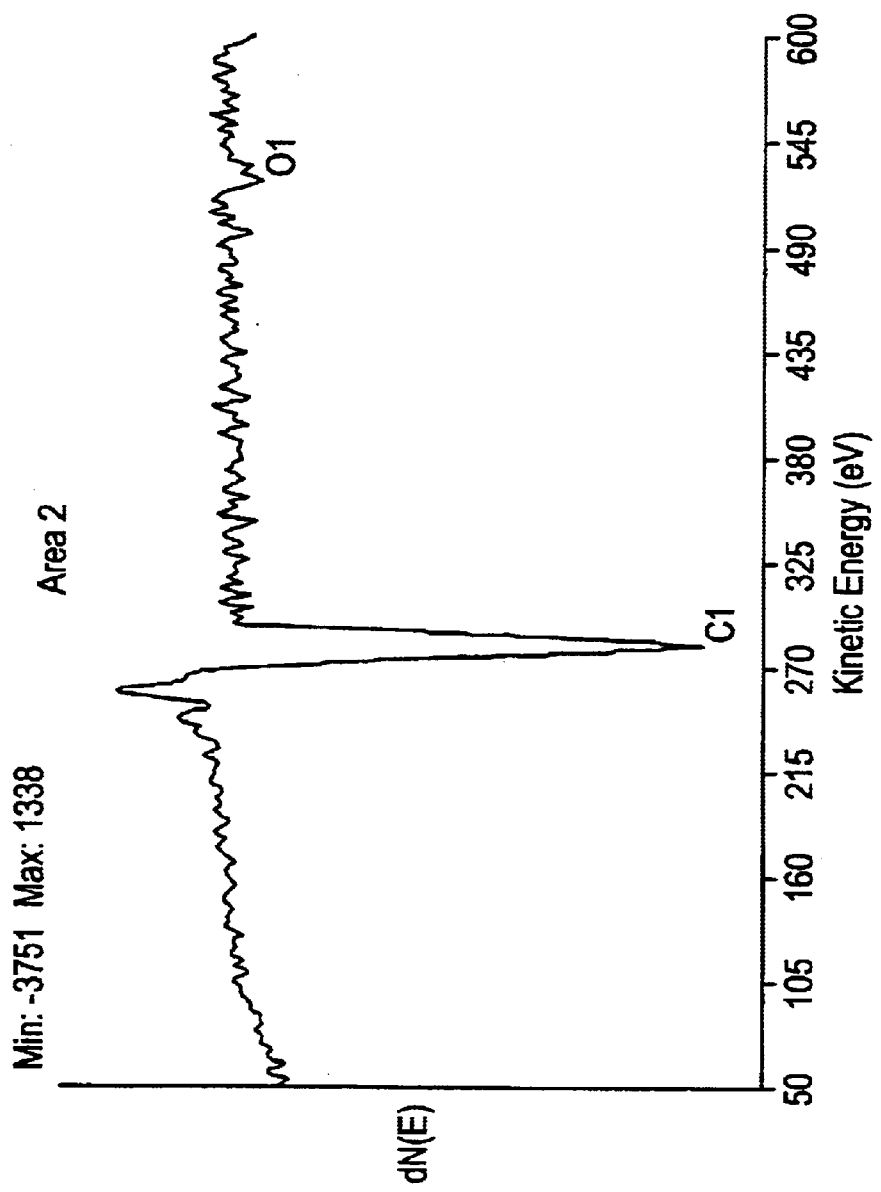
FIG. 7 illustrates an Auger scan of area 2 of FIG. 5 from implanted fingerprints.
Figure 8:
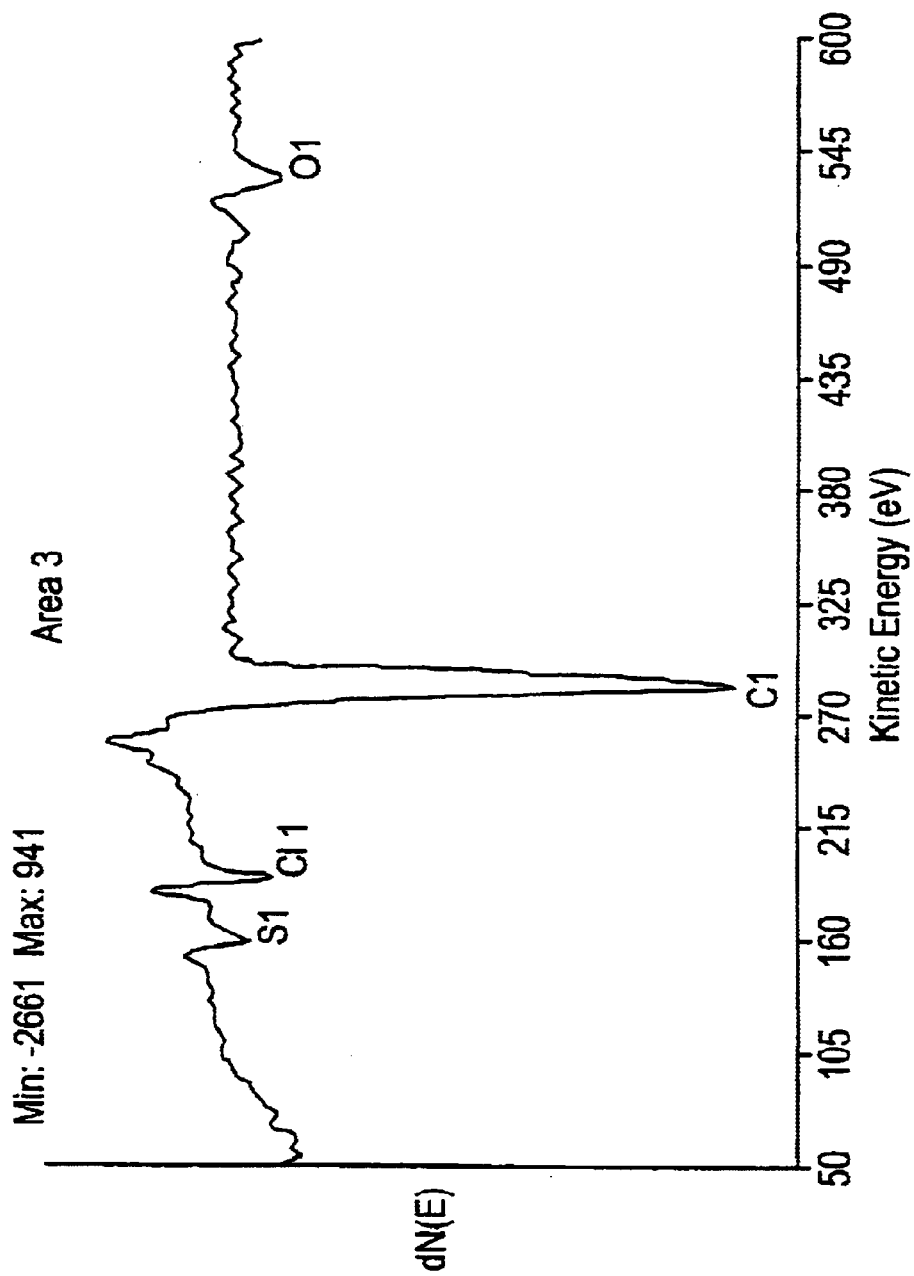
FIG. 8 illustrates an Auger scan of area 3 of FIG. 5 from the implanted fingerprints.

FIG. 5 illustrates an enlarged fingerprint 18 area with three areas marked 1, 2 and 3. These correspond to areas of the substrate 16 analyzed for chemical analysis and mapping. FIGS. 6, 7 and 8 are spectra charts for each of the points 1, 2 and 3. In FIG. 6, note the sulfur and chlorine peaks. Whereas in FIG. 7 for area 2, note the absence of sulfur and chlorine peaks. FIG. 8 for area 3 has both chlorine and sulfur peaks.

Figure 9:
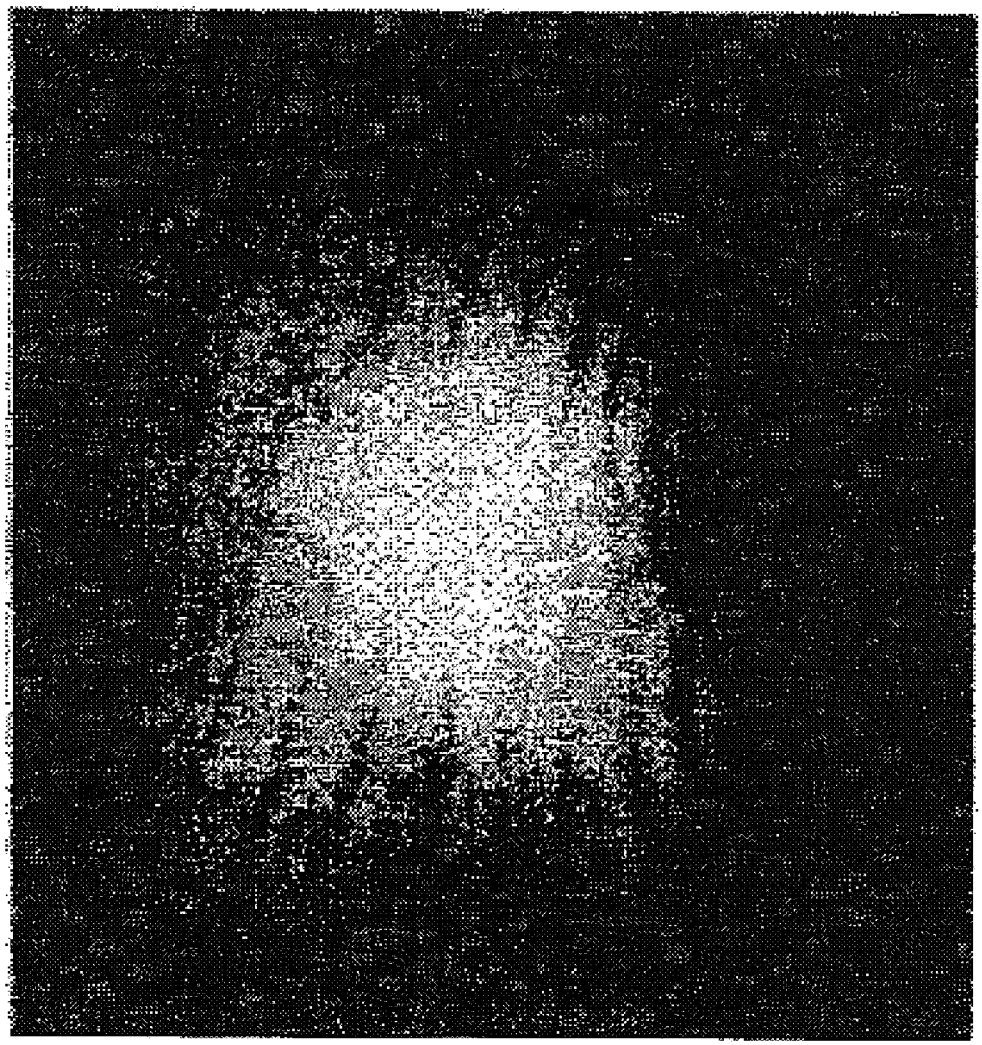
FIG. 9 illustrates a computer map of a fingerprint using an Auger signal.

FIG. 9 is an image generated from the mapping of chlorine peaks of a fingerprint 18 collected with a carbon signal at very low magnification. The image of FIG. 9 would appear on the video monitor of computer 58. The bright area in the middle is the normal collection of the detector 54. The darker area represents the non-linear response of the larger detector 54 area. It will be recognized that the Auger detector 54 could be modified to have a linear response over a larger area.

In the example of FIGS. 4–9, the spectra from the ion beam mixed fingerprint 18 were used to determine elements present on the substrate 16 that indicate presence of a fingerprint area after ion implantation. In this example, the element was selected as chlorine. It will be appreciated that other elements of the fingerprint 18 can be selected for mapping as well. In addition, or as an alternative, the spectra from the ion beam mixed fingerprint 18 can be used to map the elements of the substrate 16 to form a "negative" image of the fingerprint 18. That is, rather than mapping elements in the fingerprint 18, the elements of the substrate 16 can be mapped to produce an image of elements in the substrate 16 that are not the fingerprint 18. The positive and negative images of the fingerprint 18 may be used separately, or the two images may be combined to create an enhanced image.

Secondary Ion Mass Spectroscopy (SIMS)

In a second embodiment, the SIMS surface analysis technique is used to analyze the ion beam mixed fingerprint 18. In applying the SIMS process, an energetic primary ion beam sputters the substrate 16 surface containing the ion beam mixed fingerprint 18. Secondary ions formed in this sputtering process are extracted from the substrate 16 and analyzed in a double-focusing mass spectrometer system. The lateral distribution of the ions is maintained through the spectrometer so that the mass resolved image of the secondary ions can be projected into several types of image detectors. Alternatively, microfocusing the primary ion beam permits analysis in ion microprobe mode. A commercially available quadropole SIMS analyzer, such as that commercially available from PHI, may be used to perform the SIMS process.

There are certain substrate 16 requirements with the use of the SIMS process. The substrate 16 may include conductors and some insulators. The substrate 16 is preferably at least 2.5 cm in diameter and less than 6 mm thick. In addition the substrate 16 is preferably be vacuum compatible.

The SIMS process has some unique advantages. These include excellent detection limits, excellent depth resolution, full periodic table coverage, rapid ion image acquisition capabilities and has three-dimensional analysis depth profiling and elemental maps.

Time-of-Flight Secondary Ion Mass Spectrometry (TOF-SIMS)

In a third embodiment, the TOF-SIMS surface analysis technique is used to analyze the ion beam mixed fingerprint 18. In the TOF-SIMS method, a focused, short-pulsed primary ion beam sputters the top surface layer of the substrate 16. The secondary ions produced in this sputtering process are extracted from the substrate 16 and injected into a time-of-flight mass spectrometer. The ions are dispersed in time according to their velocity, which is proportional to their mass-to-charge ratio [m/z]. The TOF-SIMS technique is capable of detecting secondary ions produced over a large mass range (typically 0 to approximately 5000 atomic mass units) and performs this mass analysis at relatively high mass resolutions (>6000 m/m), which allows specific identification of molecules and molecular fragments with the same nominal atomic mass. When used in conjunction with a computer aided mapping interface, this technique is capable of generating a detailed image of the ion beam mixed fingerprint 18 using these molecules and molecular fragments.

The TOF-SIMS process also has certain substrate 16 requirements. The substrate 16 may be a conductor or an insulator, and is preferably of less than 200 mm diameter, is preferably less than 12.5 mm thick, and is preferably vacuum compatible.

The TOF-SIMS process also has certain unique advantages. The process is rapid, non-destructive, sensitive elemental, inorganic and organic compound analysis of top monolayer of a surface Imaging analysis of the lateral distribution of selected secondary ions. It has high mass range, resolution, and mass accuracy determinations. This technique has the potential of identifying unique chemical characteristics of the residual material from fingerprints 18.

SIMS detection limits can be in parts per million. In addition, SIMS is a mass spectrometer technique that can detect atomic species, molecules and molecular fragments. A SIMS mapping of a fingerprint 18 can be produced form trace materials such as motor oil, gunpowder or TNT. As a result, this technique could further enhance the information obtainable from the fingerprint 18 by providing another link to the person leaving it through the evidence of the materials they have handled.

Particle Induced X-Ray Emission (PIXE)

In a fourth embodiment, the PIXE surface analysis technique is used to analyze the ion beam mixed fingerprint. In this technique, a charged particle, such as a proton, interacts with atoms in the substrate 16. When a collision occurs, it results in a cascade of electrons from higher orbitals of the atoms in the substrate 16, with the subsequent emission of an X-ray equal to the energy difference between the two energy levels. This method of de-excitation is appropriately called "x-ray emission". This technique can detect concentration levels as low as parts per billion. The application of PIXE to map an ion beam mixed fingerprint 18 would further lower the detection limits and provide evidence where none is now available.

Secondary Electron Microscopy (SEM) and Energy Dispersive X-ray Spectroscopy (EDS)

In a fifth embodiment, the SEM and EDS techniques are used to analyze the ion beam mixed fingerprint 18. In the SEM technique, a finely focused electron beam is scanned across the surface of the substrate 16 to generate secondary electrons, backscattered electrons, and characteristic X-rays. These signals are then collected to form SEM images of the substrate 16. Features seen in the SEM images can then be analyzed for elemental composition using EDS. EDS is applicable for all elements with an atomic number greater than boron. Most elements can be detected at concentrations at or greater than 0.1%. In an exemplary embodiment, the commercially available Amray model 2000 may be used for the SEM/EDS analysis.

In any of the embodiments described hereinabove, it is possible to vary the computer mapping process of the substrate 16 to produce an image or facsimile of the fingerprint 18. It is probable that additional ion beam sputtering, ion beam etching of the surface layer of the substrate 16 will further reveal or enhance the ion beam mixed fingerprint 18. It is also possible to use any other analysis technique that is aided by the ion beam process, ion beam mixing, or ion implantation method. The analysis techniques discussed above may be used independently, or may be used in combination to create an enhanced image of the fingerprint 18. For example, a mapped image of the ion beam mixed fingerprint 18 using Auger electron spectroscopy technique may be combined, compared, or contrasted with a mapped image of the ion beam mixed fingerprint 18 using the SIMS surface analysis technique to create an enhanced image.

The method and apparatus described herein allow the detection of latent fingerprints at concentration levels that are orders of magnitude lower than previously possible. Because this is a computer aided atomic mapping of the ion beam mixed elements of the fingerprint, detection levels are far lower then those needed for visual identification. In certain embodiments described herein, a fingerprint can be produced form trace materials such as motor oil, gunpowder or TNT. As a result, this technique could further enhance the information obtainable from the fingerprint by providing another link to the person leaving it through the evidence of the materials they have handled. A further benefit of the ion implantation process is that the fingerprint is permanently fixed in the substrate and can serve as a long-term record.

While the invention has been described with reference to preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for this invention, but that the invention will include all embodiments falling within the scope of the appended claims.

What is claimed is:

1. A method of detecting fingerprints on a substrate, the method comprising:
   ion beam mixing materials of a latent fingerprint into the substrate to create an ion beam mixed fingerprint, such that the atoms that form the latent fingerprints become an integral part of the substrate, the ion beam mixing being performed with an ion beam having an element, an energy, and a fluence selected based on a material of the substrate; and
   analyzing the ion beam mixed fingerprint.
2. The method of claim 1, wherein the analyzing includes: optically imaging the ion beam mixed fingerprint.
3. The method of claim 1, wherein the analyzing includes: scanning the ion beam mixed fingerprint with a scanning electron microscope.
4. The method of claim 1, wherein the analyzing includes: performing a surface analysis technique on the ion beam mixed fingerprint to identify the chemical composition of at least one material associated with at least one of the fingerprint and the substrate.
5. The method of claim 4, wherein the surface analysis technique includes at least one of Auger Spectroscopy, Secondary Ion Mass Spectroscopy (SIMS), Secondary Electron Microscopy (SEM), Particle Induced X-ray Emission (PIXE), and Energy Dispersive X-ray Spectroscopy (EDS).
6. The method of claim 4, wherein the analyzing includes: mapping the chemical composition of the at least one material associated with the at least one of the fingerprint and the substrate to produce a computer generated image of the fingerprint.
7. The method of claim 6, wherein the mapping includes: identifying an element in the chemical composition of the at least one material associated with the at least one of the fingerprint and the substrate; and
   assigning pixel intensities to the relative abundance of the element in the chemical composition.
8. The method of claim 1, wherein the material of the substrate is a polymer, and the element has a cross section smaller than that of argon.
9. The method of claim 8, wherein the element is a chlorine element.
10. The method of claim 8, wherein the energy is greater than or equal to about 35 keV and less than or equal to about 200 keV.
11. The method of claim 10, wherein the energy is less than or equal to about 100 keV.
12. The method of claim 11, wherein the energy is less than or equal to about 50 keV.
13. The method of claim 10, wherein the fluence is greater than or equal to about $1 \times 10^{11}$ ions per square centimeter and less than or equal to about $5 \times 10^{19}$ ions per square centimeter.
14. The method of claim 13, wherein the fluence is greater than or equal to about $1 \times 10^{15}$ ions per square centimeter and less than or equal to about $5 \times 10^{16}$ ions per square centimeter.
15. The method of claim 1, wherein the material of the substrate is a metal, and the element is a reactive element.
16. The method of claim 15, wherein the reactive element includes one of oxygen and chlorine.
17. The method of claim 15, wherein the energy is greater than or equal to about 25 keV and less than or equal to about 200 keV.
18. The method of claim 17, wherein the energy is greater than or equal to about 40 keV and less than or equal to about 100 keV.
19. The method of claim 18, wherein the energy is greater than or equal to about 50 keV and less than or equal to about 75 keV.
20. The method of claim 17, wherein the fluence is greater than or equal to about $1 \times 10^{11}$ ions per square centimeter and less than or equal to about $1 \times 10^{19}$ ions per square centimeter.
21. The method of claim 20, wherein the fluence is greater than or equal to about $1 \times 10^{16}$ ions per square centimeter and less than or equal to about $1 \times 10^{17}$ ions per square centimeter.
22. The method of claim 21, wherein the fluence is less than or equal to about $5 \times 10^{16}$ ions per square centimeter.
23. The method of claim 1, wherein the material of the substrate is a glass, and the element has a cross section smaller than that of xenon.
24. The method of claim 23, wherein the element is lithium.
25. The method of claim 23, wherein the energy is greater than or equal to about 40 keV and less than or equal to about 200 keV.
26. The method of claim 25, wherein the energy is greater than or equal to about 50 keV and less than or equal to about 100 keV.
27. The method of claim 25, wherein the fluence is greater than or equal to about $5 \times 10^{11}$ ions per square centimeter and less than or equal to about $5 \times 10^{19}$ ions per square centimeter.
28. The method of claim 27, wherein the fluence is greater than or equal to about $5 \times 10^{16}$ ions per square centimeter and less than or equal to about $5 \times 10^{17}$ ions per square centimeter.
29. The method of claim 28, wherein the fluence is greater than or equal to about $1 \times 10^{17}$ and less than or equal to about $2 \times 10^{17}$ ions per square centimeter.
30. The method of claim 1, wherein the material of the substrate is a paper, and the element has a cross section smaller than that of argon.
31. The method of claim 30, wherein the element is lithium.
32. The method of claim 30, wherein the energy is greater than or equal to about 30 keV and less than or equal to about 200 keV.
33. The method of claim 32, wherein the energy is less than or equal to about 70 keV.
34. The method of claim 32, wherein the fluence is greater than or equal to about $1 \times 10^{11}$ ions per square centimeter and less than or equal to about $1 \times 10^{19}$ ions per square centimeter.
35. The method of claim 34, wherein the fluence is greater than or equal to about $1 \times 10^{15}$ ions per square centimeter and less than or equal to about $1 \times 10^{16}$ ions per square centimeter.

36. A system for detecting fingerprints on a substrate, the system comprising:

an ion implanter configured to provide an ion beam for ion beam mixing materials of a latent fingerprint into the substrate to create an ion beam mixed fingerprint, such that the atoms that form the latent fingerprints become an integral part of the substrate, the ion beam having an element, an energy, and a fluence selected based on a material of the substrate; and a means for analyzing the ion beam mixed fingerprint.

37. The method of claim 36, wherein the means for analyzing includes:

an optical imaging device.

38. The method of claim 36, wherein the means for analyzing includes:

a scanning electron microscope.

39. The method of claim 36, wherein the means for analyzing includes:

a system configured to perform a surface analysis technique on the ion beam mixed fingerprint to identify the chemical composition of at least one material associated with at least one of the fingerprint and the substrate.

40. The method of claim 36, wherein the system employs at least one of Auger Spectroscopy, Secondary Ion Mass Spectroscopy (SIMS), Secondary Electron Microscopy (SEM), Particle Induced X-ray Emission (PIXE), and Energy Dispersive X-ray Spectroscopy (EDS).

41. The method of claim 39, wherein the system includes:

a computer configured to map the chemical composition of the at least one material associated with the at least one of the fingerprint and the substrate and produce an image of the fingerprint.

42. The method of claim 41, wherein the computer is further configured to identify an element in the chemical composition of the at least one material associated with the at least one of the fingerprint and the substrate and assign pixel intensities to the relative abundance of the element in the chemical composition.

43. The method of claim 36, wherein the material of the substrate is a polymer, and the element has a cross section smaller than that of argon.

44. The method of claim 43, wherein the element is a chlorine element.

45. The method of claim 43, wherein the energy is greater than or equal to about 35 keV and less than or equal to about 200 keV.

46. The method of claim 45, wherein the energy is less than or equal to about 100 keV.

47. The method of claim 46, wherein the energy is less than or equal to about 50 keV.

48. The method of claim 45, wherein the fluence is greater than or equal to about $1\times10^{11}$ ions per square centimeter and less than or equal to about $5\times10^{19}$ ions per square centimeter.

49. The method of claim 48, wherein the fluence is greater than or equal to about $1\times10^{15}$ ions per square centimeter and less than or equal to about $5\times10^{16}$ ions per square centimeter.

50. The method of claim 36, wherein the material of the substrate is a metal, and the element is a reactive element.

51. The method of claim 50, wherein the reactive element includes one of oxygen and chlorine.

52. The method of claim 50, wherein the energy is greater than or equal to about 25 keV and less than or equal to about 200 keV.

53. The method of claim 52, wherein the energy is greater than or equal to about 40 keV and less than or equal to about 100 keV.

54. The method of claim 53, wherein the energy is greater than or equal to about 50 keV and less than or equal to about 75 keV.

55. The method of claim 52, wherein the fluence is greater than or equal to about $1\times10^{11}$ ions per square centimeter and less than or equal to about $1\times10^{19}$ ions per square centimeter.

56. The method of claim 55, wherein the fluence is greater than or equal to about $1\times10^{16}$ ions per square centimeter and less than or equal to about $1\times10^{17}$ ions per square centimeter.

57. The method of claim 56, wherein the fluence is less than or equal to about $5\times10^{16}$ ions per square centimeter.

58. The method of claim 36, wherein the material of the substrate is a glass, and the element has a cross section smaller than that of xenon.

59. The method of claim 58, wherein the element is lithium.

60. The method of claim 58, wherein the energy is greater than or equal to about 40 keV and less than or equal to about 200 keV.

61. The method of claim 60, wherein the energy is greater than or equal to about 50 keV and less than or equal to about 100 keV.

62. The method of claim 60, wherein the fluence is greater than or equal to about $5\times10^{11}$ ions per square centimeter and less than or equal to about $5\times10^{19}$ ions per square centimeter.

63. The method of claim 62, wherein the fluence is greater than or equal to about $5\times10^{16}$ ions per square centimeter and less than or equal to about $5\times10^{17}$ ions per square centimeter.

64. The method of claim 63, wherein the fluence is greater than or equal to about $1\times10^{17}$ and less than or equal to about $2\times10^{17}$ ions per square centimeter.

65. The method of claim 36, wherein the material of the substrate is a paper, and the element has a cross section smaller than that of argon.

66. The method of claim 65, wherein the element is lithium.

67. The method of claim 65, wherein the energy is greater than or equal to about 30 keV and less than or equal to about 200 keV.

68. The method of claim 67, wherein the energy is less than or equal to about 70 keV.

69. The method of claim 67, wherein the fluence is greater than or equal to about $1\times10^{11}$ ions per square centimeter and less than or equal to about $1\times10^{19}$ ions per square centimeter.

70. The method of claim 69, wherein the fluence is greater than or equal to about $1\times10^{15}$ ions per square centimeter and less than or equal to about $1\times10^{16}$ ions per square centimeter.

* * * * *